United States Patent
Dove et al.

(10) Patent No.: US 12,076,141 B2
(45) Date of Patent: Sep. 3, 2024

(54) SYSTEM AND METHOD FOR DIGITALLY CALIBRATING A MEDICAL SENSOR

(71) Applicant: Covidien LP, Mansfield, MA (US)

(72) Inventors: Jacob D. Dove, Lafayette, CO (US); Christopher J. Meehan, Denver, CO (US)

(73) Assignee: COVIDIEN LP, Mansfield, MA (US)

( * ) Notice: Subject to any disclaimer, the term of this patent is extended or adjusted under 35 U.S.C. 154(b) by 342 days.

(21) Appl. No.: 17/186,262

(22) Filed: Feb. 26, 2021

(65) Prior Publication Data
US 2022/0273206 A1    Sep. 1, 2022

(51) Int. Cl.
*A61B 5/1455* (2006.01)
*A61B 5/1495* (2006.01)

(52) U.S. Cl.
CPC ...... *A61B 5/14552* (2013.01); *A61B 5/14551* (2013.01); *A61B 5/1495* (2013.01); *A61B 2560/0223* (2013.01)

(58) Field of Classification Search
CPC ............ A61B 5/14552; A61B 5/14551; A61B 5/1495; A61B 2560/0223; A61B 5/145
See application file for complete search history.

(56) References Cited

U.S. PATENT DOCUMENTS

| | | |
|---|---|---|
| 7,343,186 B2 | 3/2008 | Lamego et al. |
| 7,392,074 B2 | 6/2008 | Isaacson et al. |
| 7,606,606 B2 | 10/2009 | Laakkonen |
| 8,145,287 B2 * | 3/2012 | Diab ............... G01J 3/0291 600/323 |
| 8,315,682 B2 | 11/2012 | Such et al. |
| 8,401,605 B2 | 3/2013 | Huiku |
| 8,720,249 B2 | 5/2014 | Al-Ali |
| 8,740,808 B2 | 6/2014 | Curti et al. |
| 8,781,544 B2 | 7/2014 | Al-Ali et al. |
| 9,107,625 B2 | 8/2015 | Telfort et al. |
| 9,125,606 B2 | 9/2015 | Verkruijsse et al. |
| 9,265,456 B2 | 2/2016 | Kirenko et al. |
| 9,341,565 B2 | 5/2016 | Lamego et al. |
| 9,364,175 B2 | 6/2016 | Benni |
| 9,649,055 B2 | 5/2017 | Ashe et al. |
| 9,693,717 B2 | 7/2017 | Benni et al. |
| 9,770,197 B2 | 9/2017 | Bresch et al. |
| 9,770,213 B2 | 9/2017 | Kirenko et al. |
| 9,801,556 B2 | 10/2017 | Kiani |
| 9,839,381 B1 | 12/2017 | Weber et al. |

(Continued)

FOREIGN PATENT DOCUMENTS

WO    2013077808 A1    5/2013

OTHER PUBLICATIONS

International Search Report for International Applicaton No. PCT/US2022/017799; Application Filing Date: Feb. 25, 2022; Date of Search: May 13, 2022; Date of Mailing: May 25, 2022, 5 pages.

(Continued)

*Primary Examiner* — Eric F Winakur
*Assistant Examiner* — Abid A Mustansir
(74) *Attorney, Agent, or Firm* — Fletcher Yoder, P.C.

(57) ABSTRACT

The present disclosure provides systems and methods for calibrating a medical device utilizing LED emission by characterizing the spectrum distribution of the LED emission and mapping such characterized spectrum distribution to calibration coefficients, e.g., gamma coefficients.

20 Claims, 12 Drawing Sheets

(56) References Cited

U.S. PATENT DOCUMENTS

| | | | |
|---|---|---|---|
| 9,980,650 | B2 | 5/2018 | Bezemer |
| 10,039,455 | B2 | 8/2018 | Lading et al. |
| 10,064,562 | B2 | 9/2018 | Al-Ali |
| 10,092,200 | B2 | 10/2018 | Al-Ali et al. |
| 10,313,137 | B2 | 6/2019 | Aarnio et al. |
| 10,531,820 | B2 | 1/2020 | De Haan et al. |
| 10,646,167 | B2 | 5/2020 | De Haan |
| 10,918,321 | B2 | 2/2021 | Benni |
| 10,993,644 | B2 | 5/2021 | Huiku et al. |
| 11,123,023 | B2 | 9/2021 | Babaeizadeh |
| 11,147,518 | B1 | 10/2021 | Al-Ali et al. |
| 11,202,582 | B2 | 12/2021 | Verkruijsse et al. |
| 11,564,630 | B2 | 1/2023 | Huiku et al. |
| 11,653,862 | B2 | 5/2023 | Dalvi et al. |
| 11,839,470 | B2 | 12/2023 | Kiani et al. |
| 2009/0247852 | A1 | 10/2009 | Boyce et al. |
| 2012/0179011 | A1 | 7/2012 | Moon et al. |
| 2014/0275890 | A1* | 9/2014 | Meehan ............... A61B 5/0002 600/324 |
| 2017/0273560 | A1 | 9/2017 | Ballam et al. |
| 2019/0175030 | A1 | 6/2019 | Verkruijsse et al. |
| 2019/0209025 | A1 | 7/2019 | Al-Ali |
| 2021/0219884 | A1 | 7/2021 | De Haan |
| 2023/0015851 | A1 | 1/2023 | Verkruijsse et al. |
| 2023/0125960 | A1 | 4/2023 | Weber et al. |

OTHER PUBLICATIONS

Written Opinion for International Applicaton No. PCT/US2022/017799; Application Filing Date: Feb. 25, 2022; Date of Search: May 13, 2022; Date of Mailing: May 25, 2022, 6 pages.

* cited by examiner

SYSTEM AND METHOD FOR DIGITALLY CALIBRATING A MEDICAL SENSOR

FIELD

The present disclosure relates generally to medical devices, and more particularly to digital calibration of medical devices that monitor physiological parameters of a patient, such as pulse oximeters.

BACKGROUND

In the field of medicine, doctors often desire to monitor certain physiological characteristics of their patients. Accordingly, a wide variety of devices have been developed for monitoring many such physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient uses attenuation of light to determine physiological characteristics of a patient. This is used in pulse oximetry, and the devices built based upon pulse oximetry techniques. Light attenuation is also used for regional or cerebral oximetry. Oximetry may be used to measure various blood characteristics, such as the oxygen saturation of hemoglobin in blood or tissue, the volume of individual blood pulsations supplying the tissue, and/or the rate of blood pulsations corresponding to each heartbeat of a patient. The signals can lead to further physiological measurements, such as respiration rate, glucose levels or blood pressure.

Pulse oximetry is often used to noninvasively measure arterial blood oxygenation. To measure blood oxygenation, two optical sources, typically light-emitting-diodes (LEDs), may be used to inject light into the tissue. A photo-diode is used to capture the light after propagating through blood perfused tissue. During a cardiac cycle, the amount of blood in the optical path changes which changes the amount the light that is absorbed. The resulting photocurrent form the photodiode is modulated. As blood oxygenation changes, the relative change in the modulated light at two distinct wavelengths changes. This relative change in the modulated photocurrent is processed (e.g., via signal conditioning, various algorithms) by the oximetry unit to estimate the arterial functional oxygenation ($SpO_2$).

To make accurate and precise measurements of $SpO_2$, it is helpful to characterize the components of the system that can lead to changes in the photocurrent produced by the photodiode. For example, if the distribution of optical flux from the LED changes, the photocurrent from the photodiode will change as well. LED-to-LED variability is typical during manufacture and is important to characterize. In addition, the efficiency of the photodetector to convert light to current is wavelength dependent, referred to as responsivity. Hence, changes in detector responsivity can lead to fluctuations in the photocurrent.

Calibration methods that utilize a single spectral characteristic, such as centroid wavelength parameter or the peak wavelength from LED emission fail to capture the full variability of LED-to-LED optical flux. However, the art would benefit from improved techniques for sensor calibration.

What is needed in the art is improved techniques to digitally calibrate pulse oximeter sensors.

SUMMARY

The techniques of this disclosure generally relate to digital calibration of medical devices that monitor physiological parameters of a patient, such as pulse oximeters.

In one aspect, the present disclosure provides systems and methods for calibrating a medical device utilizing LED emission by characterizing the spectrum distribution of the LED emission and mapping such characterized spectrum distribution to calibration coefficients, e.g., gamma coefficients.

In exemplary embodiments, the LED emission provides an asymmetric distribution; and mapping of the characterized spectrum distribution to one or more calibration coefficients reflects such asymmetric distribution.

In further exemplary embodiments, the full spectrum distribution of an LED is characterized, with mapping of the characterized full spectrum distribution to one or more calibration coefficients reflects such full spectrum distribution.

Exemplary embodiments of the present disclosure improve mapping from an LED emission spectrum to gamma coefficients by performing one or more of the following techniques: de-convolving LED distribution into N Gaussian distributions, using the Gaussian distribution to map LEDs to gammas; fitting an LED distribution to a logistic power peak and using the fitted parameters to map LEDs to gammas; fitting an LED distribution to an asymmetric double sigmoidal and mapping LEDs to gammas; characterizing distribution skewness; measuring the peak wavelength and/or FWHM in addition to centroid wavelength and mapping to gammas; and integrating LED distribution with a blood absorption curve and mapping to gammas.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

The present disclosure describes systems and methods for improved oximeter sensor calibration by assessing the characteristics of LED emission. As will be described in more detail below, the present disclosure provides systems and methods for calibrating a medical device utilizing one or more LEDs by characterizing the spectrum distribution of the LED emission and mapping such characterized spectrum distribution to calibration coefficients, e.g., gamma coefficients, which may be used in exemplary embodiments to convert ratio-of-ratio values to $SpO_2$ values.

In exemplary embodiments, the LED emission provides an asymmetric distribution; and mapping of the characterized spectrum distribution to one or more calibration coefficients reflects such asymmetric distribution.

In further exemplary embodiments, the full spectrum distribution of an LED is characterized, with mapping of the characterized full spectrum distribution to one or more calibration coefficients reflects such full spectrum distribution.

Figure 1:
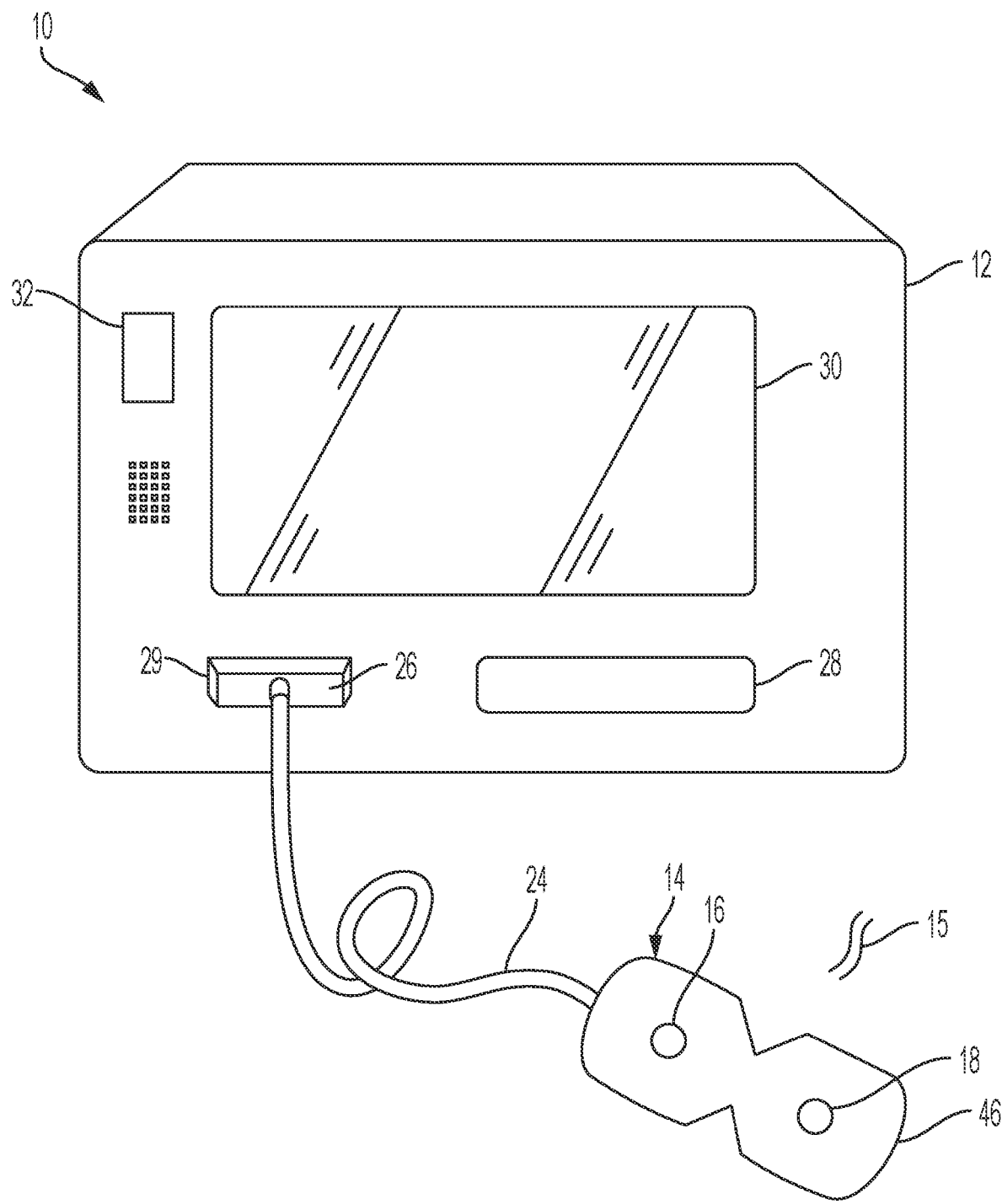
FIG. 1 illustrates a perspective view of an exemplary patient monitoring system including a patient monitor and a patient monitoring sensor, in accordance with an embodiment.

FIG. 1 illustrates an embodiment of a patient monitoring system 10 that includes a patient monitor 12 and a sensor 14, such as a pulse oximetry sensor, to monitor physiological parameters of a patient. By way of example, the sensor 14 may be a NELLCOR™, or INVOS™ sensor available from Medtronic (Boulder, CO), or another type of oximetry sensor. Although the depicted embodiments relate to sensors for use on a patient's fingertip, toe, or earlobe, it should be understood that, in certain embodiments, the features of the sensor 14 as provided herein may be incorporated into sensors for use on other tissue locations, such as the forehead and/or temple, the heel, stomach, chest, back, or any other appropriate measurement site.

In the embodiment of FIG. 1, the sensor 14 is a pulse oximetry sensor that includes one or more emitters 16 and one or more detectors 18. For pulse oximetry applications, the emitter 16 transmits at least two wavelengths of light (e.g., red and/or infrared (IR)) into a tissue of the patient. For other applications, the emitter 16 may transmit 3, 4, or 5 or more wavelengths of light into the tissue of a patient. The detector 18 is a photodetector selected to receive light in the range of wavelengths emitted from the emitter 16, after the light has passed through the tissue. Additionally, the emitter 16 and the detector 18 may operate in various modes (e.g., reflectance or transmission). In certain embodiments, the sensor 14 includes sensing components in addition to, or instead of, the emitter 16 and the detector 18.

The sensor 14 also includes a sensor body 46 to house or carry the components of the sensor 14. In exemplary embodiments, the body 46 includes a backing, or liner, provided around the emitter 16 and the detector 18, as well as an adhesive layer (not shown) on the patient side. The sensor 14 may be reusable (such as a durable plastic clip sensor), disposable (such as an adhesive sensor including a bandage/liner at least partially made from hydrophobic materials), or partially reusable and partially disposable.

In the embodiment shown, the sensor 14 is communicatively coupled to the patient monitor 12. In certain embodiments, the sensor 14 may include a wireless module configured to establish a wireless communication 15 with the patient monitor 12 using any suitable wireless standard. For example, the sensor 14 may include a transceiver that enables wireless signals to be transmitted to and received from an external device (e.g., the patient monitor 12, a charging device, etc.). The transceiver may establish wireless communication 15 with a transceiver of the patient monitor 12 using any suitable protocol. For example, the transceiver may be configured to transmit signals using one or more of the ZigBee standard, 802.15.4x standards WirelessHART standard, Bluetooth standard, IEEE 802.11x standards, or MiWi standard. Additionally, the transceiver may transmit a raw digitized detector signal, a processed digitized detector signal, and/or a calculated physiological parameter, as well as any data that may be stored in the sensor, such as calibration data or coefficients, such as gamma coefficients, data relating to wavelengths of the emitters 16, or data relating to input specification for the emitters 16, as discussed below. Additionally, or alternatively, the emitters 16 and detectors 18 of the sensor 14 may be coupled to the patient monitor 12 via a cable 24 through a plug 26 (e.g., a connector having one or more conductors) coupled to a sensor port 29 of the monitor. In certain embodiments, the sensor 14 is configured to operate in both a wireless mode and a wired mode. Accordingly, in certain embodiments, the cable 24 is removably attached to the sensor 14 such that the sensor 14 can be detached from the cable to increase the patient's range of motion while wearing the sensor 14.

The patient monitor 12 is configured to calculate physiological parameters of the patient relating to the physiological signal received from the sensor 14. For example, the patient monitor 12 may include a processor configured to calculate the patient's arterial blood oxygen saturation, tissue oxygen saturation, pulse rate, respiration rate, blood pressure, blood pressure characteristic measure, autoregulation status, brain activity, and/or any other suitable physiological characteristics. Additionally, the patient monitor 12 may include a monitor display 30 configured to display information regarding the physiological parameters, information about the system (e.g., instructions for disinfecting and/or charging the sensor 14), and/or alarm indications. The patient monitor 12 may include various input components 32, such as knobs, switches, keys and keypads, buttons, etc., to provide for operation and configuration of the patient monitor 12. The patient monitor 12 may also display information related to alarms, monitor settings, and/or signal quality via one or more indicator lights and/or one or more speakers or audible indicators. The patient monitor 12 may also include an upgrade slot 28, in which additional modules can be inserted so that the patient monitor 12 can measure and display additional physiological parameters.

Because the sensor 14 may be configured to operate in a wireless mode and, in certain embodiments, may not receive power from the patient monitor 12 while operating in the wireless mode, the sensor 14 may include a battery to provide power to the components of the sensor 14 (e.g., the emitter 16 and the detector 18). In certain embodiments, the battery may be a rechargeable battery such as, for example, a lithium ion, lithium polymer, nickel-metal hydride, or nickel-cadmium battery. However, any suitable power source may be utilized, such as, one or more capacitors and/or an energy harvesting power supply (e.g., a motion generated energy harvesting device, thermoelectric generated energy harvesting device, or similar devices).

As noted above, in an embodiment, the patient monitor 12 is a pulse oximetry monitor and the sensor 14 is a pulse oximetry sensor. The sensor 14 may be placed at a site on a patient with pulsatile arterial flow, typically a fingertip, toe, forehead or earlobe, or in the case of a neonate, across a foot. Additional suitable sensor locations include, without limitation, the neck to monitor carotid artery pulsatile flow, the wrist to monitor radial artery pulsatile flow, the inside of a patient's thigh to monitor femoral artery pulsatile flow, the ankle to monitor tibial artery pulsatile flow, and around or in front of the ear. The patient monitoring system 10 may include sensors 14 at multiple locations. The emitter 16 emits light which passes through the blood perfused tissue, and the detector 18 photoelectrically senses the amount of light reflected or transmitted by the tissue. The patient monitoring system 10 measures the intensity of light that is received at the detector 18 as a function of time.

A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The amount of light detected or absorbed may then be used to calculate any of a number of physiological parameters, including oxygen saturation (the saturation of oxygen in pulsatile blood, SpO2), an amount of a blood constituent (e.g., oxyhemoglobin), as well as a physiological rate (e.g., pulse rate or respiration rate) and when each individual pulse or breath occurs. For SpO2, red and infrared (IR) wavelengths may be used because it has been observed that highly oxygenated blood will absorb relatively less Red light and more IR light than blood with a lower oxygen saturation. By comparing the intensities of two wavelengths at different points in the pulse cycle, it is possible to estimate the blood oxygen saturation of hemoglobin in arterial blood, such as from empirical data that may be indexed by values of a ratio, a lookup table, and/or from curve fitting and/or other interpolative techniques.

Figure 2:
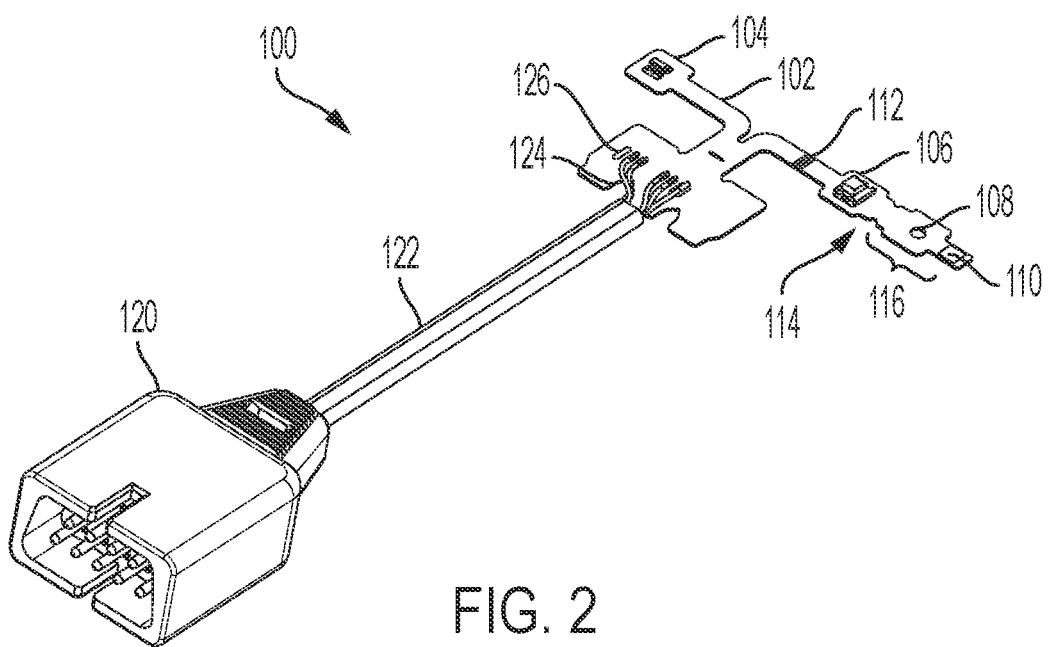
FIG. 2 illustrates a perspective view of an exemplary patient monitoring sensor.

Referring now to FIG. 2, an embodiment of a patient monitoring sensor 100 in accordance with an embodiment is shown. As may be seen, the shape or profile of various components may vary. The sensor 100 includes a body 102 that includes a flexible circuit. The sensor 100 includes one or more LEDs 104 (in this case a surface mount LED package with two LEDs) and one or more detectors 106 disposed on the body 102 of the sensor 100.

While any number of exemplary sensor designs are contemplated herein, in the illustrated exemplary embodiment, the body 100 includes a flap portion 116 that includes an aperture 108. The flap portion 116 is configured to be folded at a hinge portion 114 such that the aperture 108 overlaps the detector 106 to allow light to pass through. In one embodiment, the flap portion 116 includes an adhesive 110 that is used to secure the flap portion 116 to the body 102 after the flap portion 116 is folded at the hinge portion 114 using visual indicator 112 that is used to assure proper alignment of the flap portion 116 when folded at the hinge portion 114.

The sensor 100 includes a plug 120 that is configured to be connected to a patient monitoring system, such as the one shown in FIG. 1. The sensor 100 also includes a cable 122 that connects the plug 120 to the body 102 of the sensor 100. The cable 122 includes a plurality of wires 124 that connect various parts of the plug 120 to terminals 126 disposed on the body 102. The flexible circuit is disposed in the body 102 and connects the terminals 126 to the LED 104 and the detector 106. In addition, one of the terminals 126 connect a ground wire to the flexible circuit.

Figure 3:
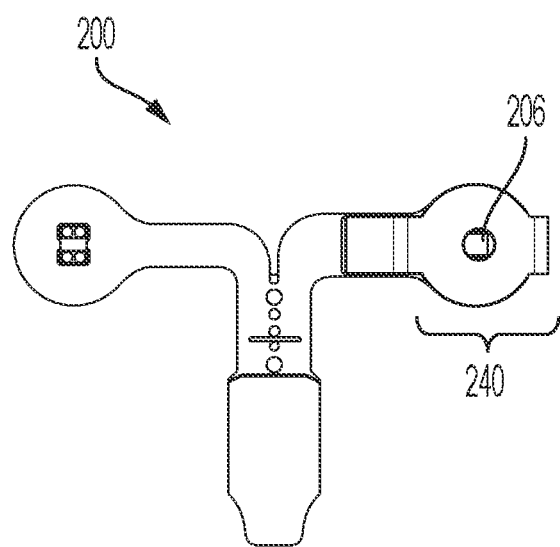
FIG. 3 illustrates a top elevation view of a portion of an assembled exemplary patient monitoring sensor.

Referring now to FIG. 3, a patient monitoring sensor 200 in accordance with an embodiment is shown. In exemplary embodiments, a faraday cage 240 is formed around the detector 206 by folding the flap portion 116 over a portion of the body 102 of the sensor 200.

Figure 4:
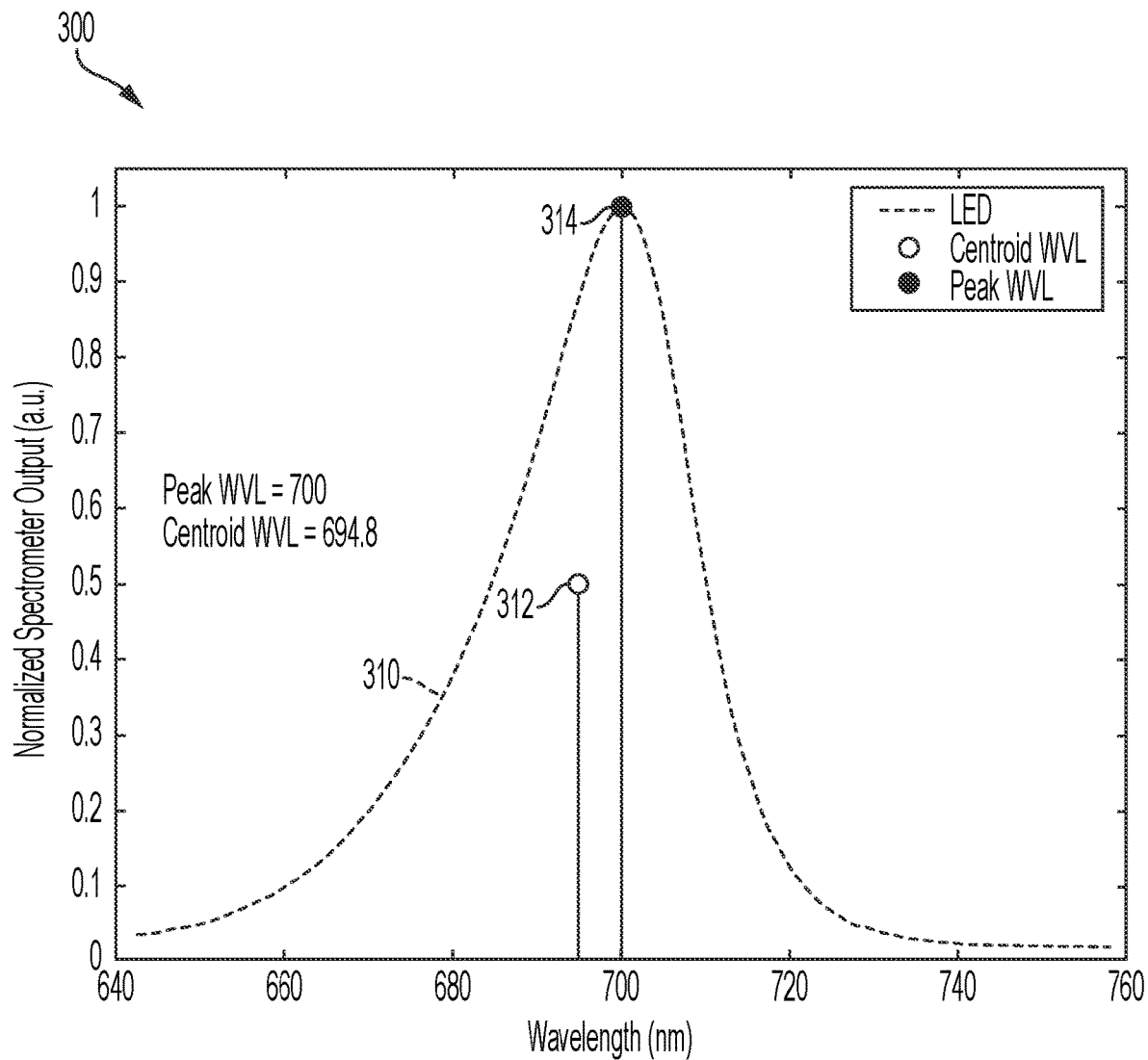
FIG. 4 is an exemplary graph of normalized spectral flux from an LED.

FIG. 4 illustrates generally at 300 an exemplary graph of normalized spectral flux from an LED (for example a red LED) as normalized spectrometer output 310 (in absorbance units (a.u.)) vs wavelength (in nanometers (nm)). As may be seen from the Figure, the emitted optical flux from an LED is not Gaussian, but instead includes a skewness. The centroid wavelength, shown at 312, is the wavelength representing the mean spectral power distribution, which may be determined using the following equation:

$$\lambda_c = \frac{\int \lambda \phi(\lambda) d\lambda}{\int \phi(\lambda) d\lambda},$$

where $\lambda_c$ is the centroid wavelength and $\Phi(\lambda)$ is the spectral power distribution of the LED.

In theory, in an LED with a symmetric spectral power distribution, the centroid, mean, and peak wavelengths would all be the same. However, as can be seen from FIG. 4, an LED may have some asymmetry. In the illustrated exemplary embodiment of FIG. 4, the centroid wavelength 312 is at wavelength A (red LEDs generally emit between 620 nm and 700 nm), and the peak wavelength 314 is at wavelength B, where the peak wavelength is greater than the centroid wavelength (for example 4-5 nm greater, though that difference may be more or less). Because the illustrated peak wavelength is greater than the centroid wavelength, FIG. 4 indicates that more of the optical output of the LED is at the shorter wavelengths than the longer wavelengths.

It can be seen that use of centroid wavelength does not capture the full distribution of the LED and is not the only important parameter. In this disclosure, the benefit of accounting for the full spectral distribution will be shown and methods to characterize the full spectral distribution so that they can be mapped to calibration coefficients will be presented.

A theoretical model may be used to explore the asymmetric distribution of light form an LED. To model the ratio of ratio, the following equation may be used.

$$R = \frac{(\ln(I_{out}(t_2)) - \ln(I_{out}(t_1)))_{\lambda_1}}{(\ln(I_{out}(t_2)) - \ln(I_{out}(t_1)))_{\lambda_2}}$$

Here, R is the ratio of ratios and the measurement of light exiting the tissue ($I_{out}$) of and is made at two different time points, $t_1$ and $t_2$ and at two wavelengths $\lambda_1$ and $\lambda_2$. The light exiting tissue, $I_{out}$, is modeled in following equation:

$$I_{out}(t) = \int I(\lambda)d\lambda - \int \mu_{blood} * ctHb(t) * l(t) * I(\lambda)d\lambda$$

Figure 5:
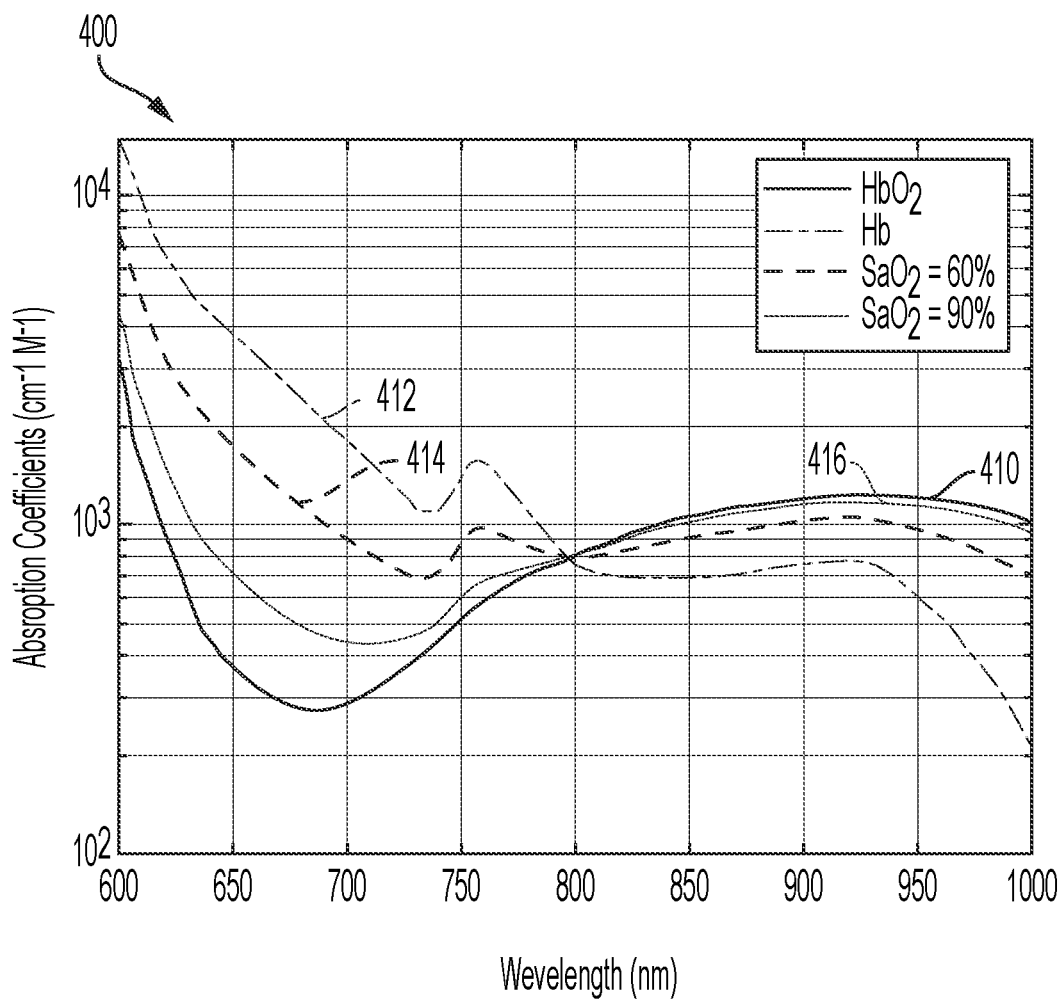
FIG. 5 is an exemplary graph of an optical absorption coefficient of blood.

Here, I is the optical intensity of the LED (or the light entering the tissue), $\mu_{blood}$ is the optical absorption of the blood, ctHb(t) is the concentration of hemoglobin, and l is the path length at the wavelength. The optical absorption coefficient of blood is shown generally at 400 in FIG. 5. The optical absorption coefficient of oxy and deoxy-hemoglobin are illustrated by lines 410 and 412, respectively. The absorption coefficient at two different saturation levels are illustrated, with dashed line 414 at 60% and dotted line 416 at 90%.

To understand the effect of skew and FWHM, an asymmetric double sigmoidal function may be used to model the LED spectral emission, the function is shown in the following equation:

$$f(\lambda) = \frac{A}{1 + e^{\frac{\lambda - C + W/2}{S_1}}} \left(1 - \frac{1}{1 + e^{\frac{\lambda - C - W/2}{S_2}}}\right)$$

Figures 6A, 6B:
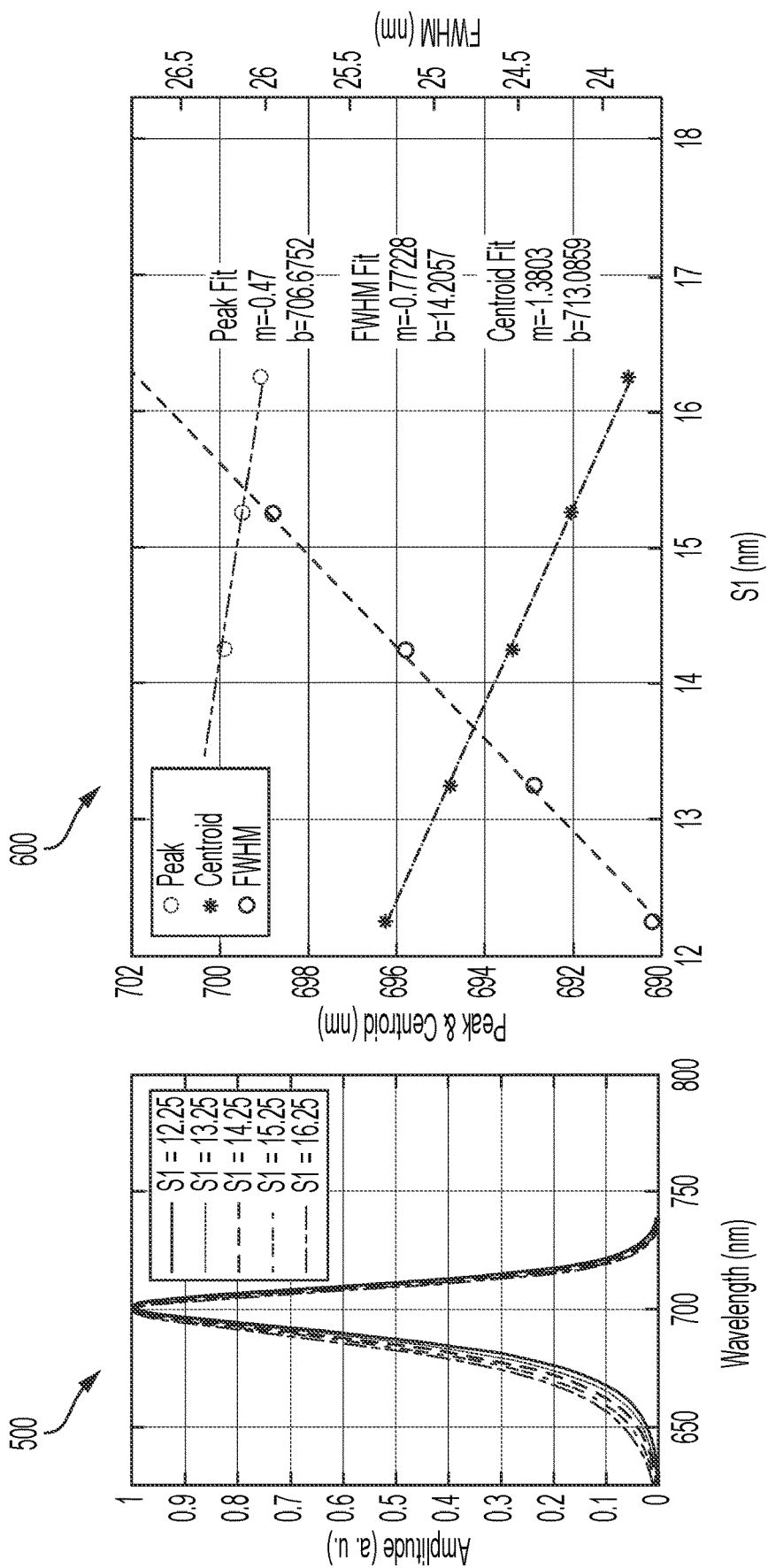
FIG. 6A is an exemplary graph illustrating the effects of changing S1 in an asymmetric double sigmoidal function.
FIG. 6B is an exemplary graph illustrating the effect of S1 on peak and centroid wavelengths.

The amplitude may be adjusted such that the total spectral flux is 1 mW. The values for C, W, S1, and S2 may be determined by fitting to a measured spectral emission. The effect of changing S1 is shown generally at 500 in FIG. 6A and 600 in FIG. 6B.

Figure 7A:
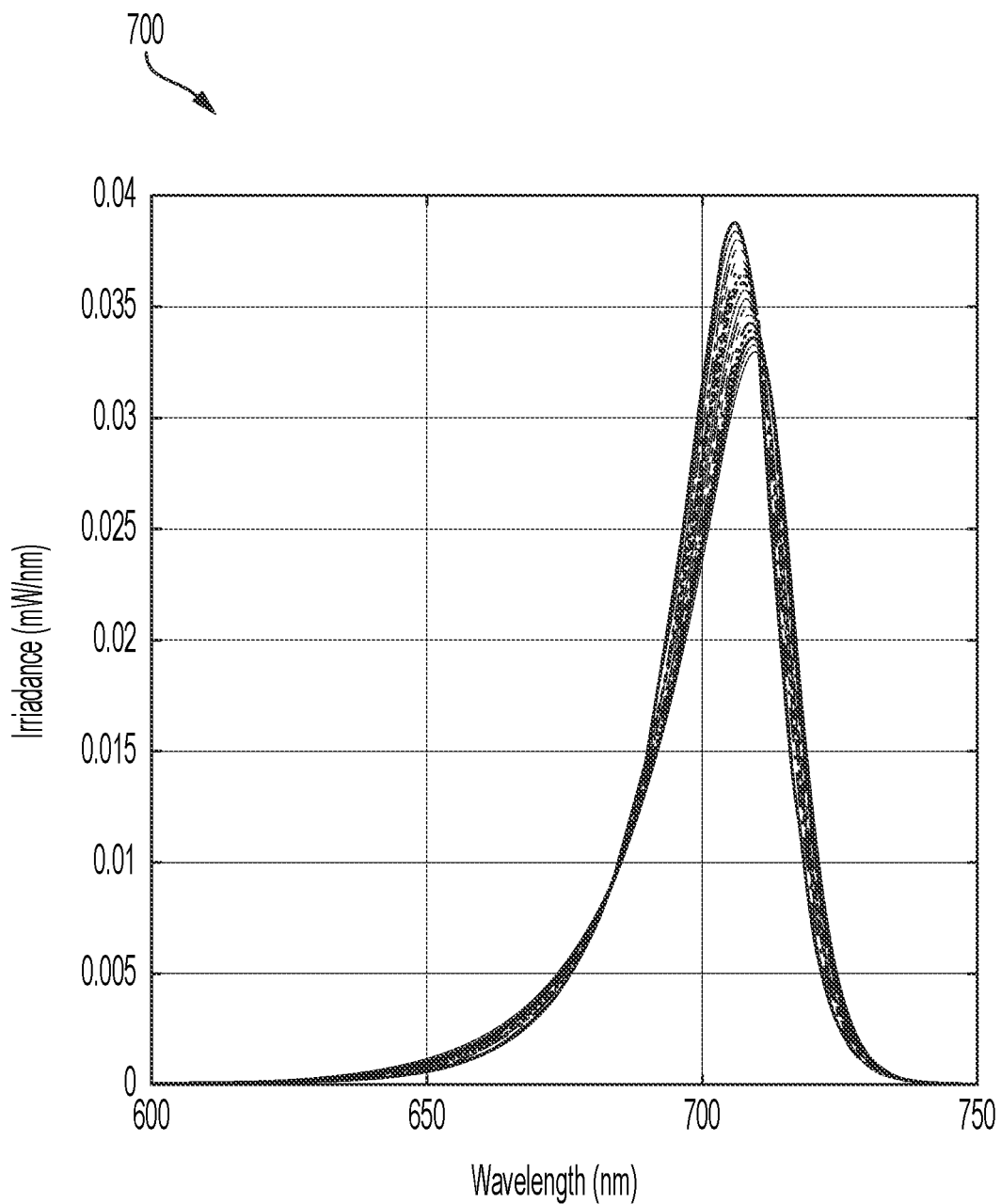
FIG. 7A is an exemplary graph illustrating the effect on spectral emission due to changing skewness.
Figure 7B:
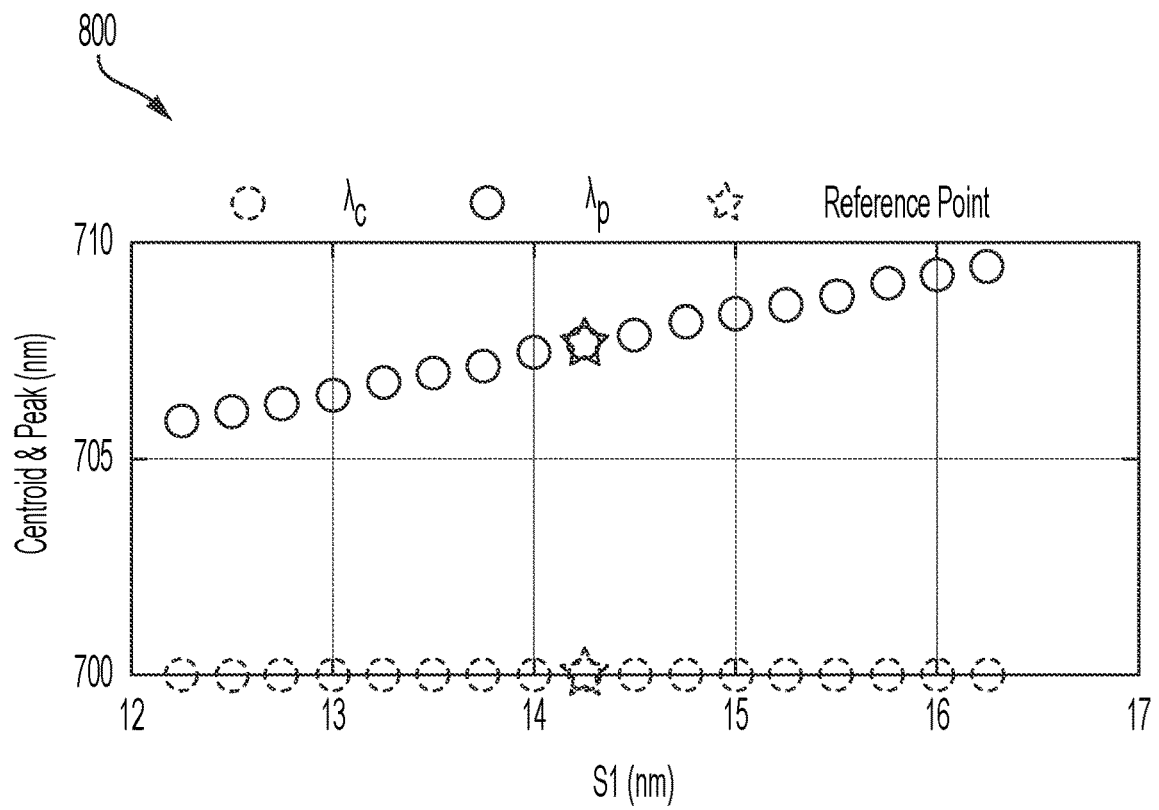
FIG. 7B is an exemplary graph illustrating change in peak wavelength but not centroid wavelength.
Figure 7C:
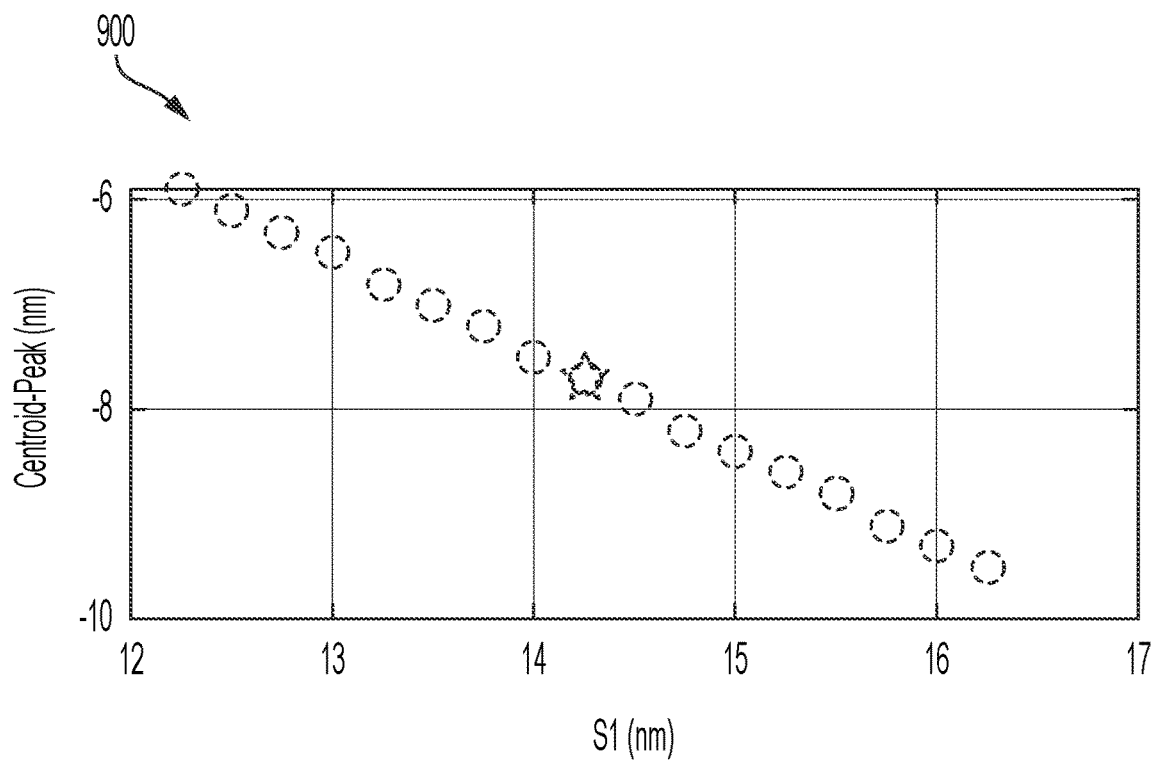
FIG. 7C is an exemplary graph illustrating change in skewness (centroid minus peak wavelength)
Figure 7D:
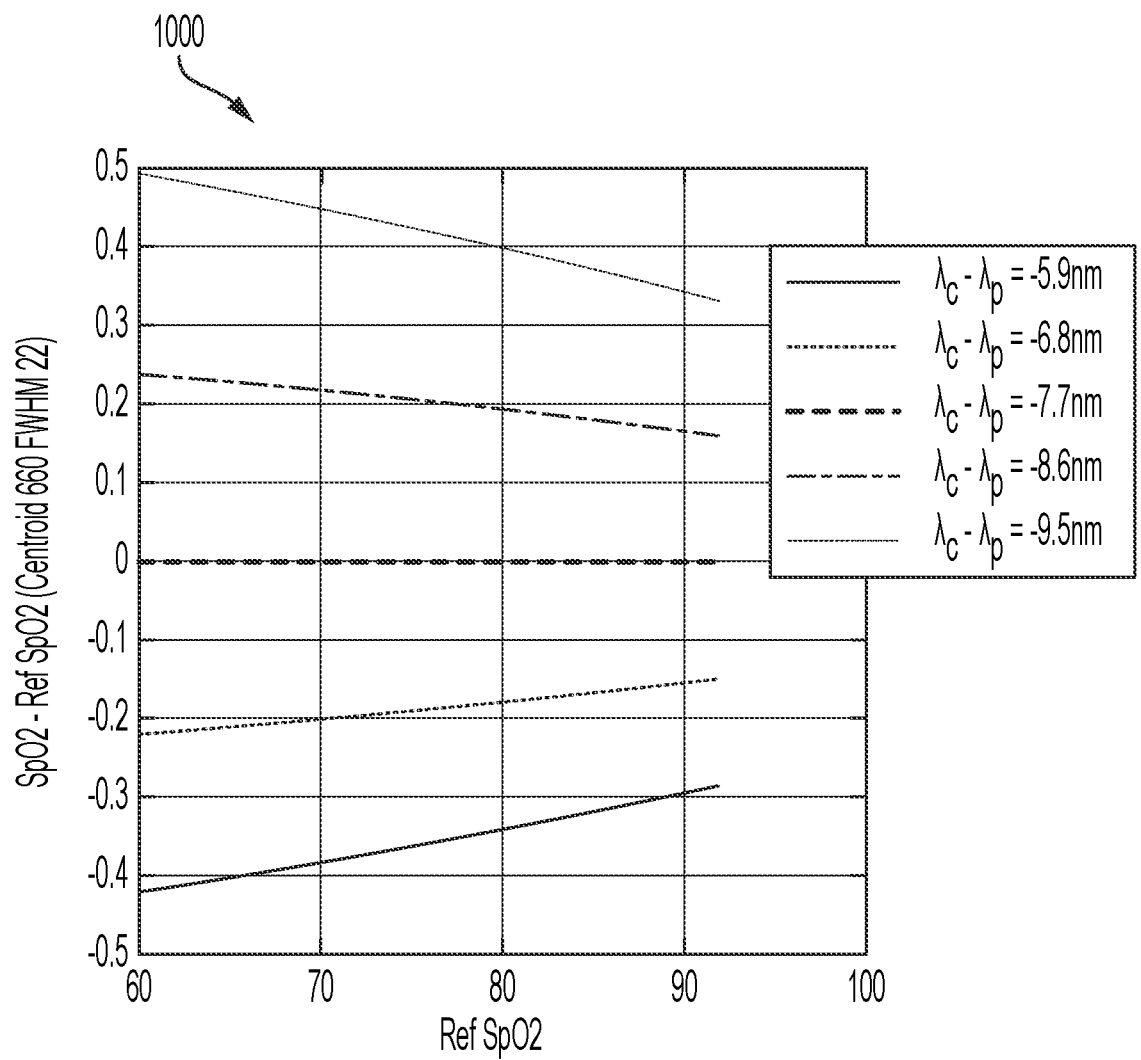
FIG. 7D is an exemplary graph illustrating the difference in $SpO_2$ due to the skewness.

S1 mostly impacts shorter wavelengths, but also effects changing the peak, centroid, and FWHM. To understand how skew and wavelengths relate, S1 and C may be altered such that the centroid wavelength is always the same, but skewness changes (which can be seen as the difference between peak and centroid), as per FIG. 7A, which shows the effect on SpO2 due to changing skewness, but not centroid wavelength. FIG. 7A shows the spectral emission generally at 700. FIGS. 7B and 7C show generally at 800 and 900 that the centroid does not change and is constant at 700 nm, but the peak wavelength does change. FIG. 7D shows generally at 1000 the difference in SpO2 due to the skewness.

Here, a 1.8 nm shift in peak verse centroid produced approximately 0.4 RMSD. Note that centroid corrections are about twice important where a 2 nm shift in centroid produces approximately 1 RMSD. Hence, it is important to characterize the full distribution of the spectral emission and not just the centroid.

Accordingly, exemplary embodiments of the present disclosure improve mapping from an LED emission spectrum to gamma coefficients. In exemplary embodiments, the present system and method may perform one or more of the following: de-convolve LED distribution into N Gaussian distributions, using the Gaussian distribution to map LEDs to gammas; fit an LED distribution to a logistic power peak and use the fitted parameters to map LEDs to gammas; fit an LED distribution to an asymmetric double sigmoidal and map LEDs to gammas; characterize distribution skewness; measure the peak wavelength and/or FWHM in addition to centroid wavelength and map to gammas; and integrate LED distribution with a blood absorption curve and map to gammas.

Exemplary aspects of the present disclosure improve accuracy to blood (SaO$_2$) for SpO$_2$, improving digital calibration by accounting for the full spectral emission. The methods disclosed outline how to characterize the full spectral emission. Once characterized, the output parameters may be mapped to calibration coefficients determined, e.g., during a hypoxia study.

With further regard to de-convolving an LED into 3 Gaussian distributions, an LED may be considered as three symmetric (Gaussian or normal distribution) LEDs instead of one. These three LEDs may be mapped to the calibration coefficients instead of just the centroid of the one emission. Mapping the LED can have all three parameters used to describe a Gaussian distribution: mean, FWHM (full width at half maximum), and amplitude; or it can have various combinations (e.g., mean and FWHM). This technique may be applied with regard to a red LED and/or an IR LED.

With further regard to fitting an LED, as will be described in more detail below, different functions may be utilized to accurately fit the LED distribution, for example, the logistic power peak and the asymmetric double sigmoidal. The fitted parameters may then be used to map to the calibration coefficients.

With further regard to characterizing the skewness of the distribution (in addition to the centroid), the technique may include measuring the peak wavelength and looking at the difference in peak verse centroid. Other exemplary methods may also be used, such as calculating kurtosis, and/or skewness (such as Pearson's moment coefficient of skewness or Pearson's first or second skewness coefficient).

With further regard to integrating LED distribution with blood absorption curve, the LED spectral distribution can be numerically integrated with the absorption curve. The resulting summation can be used to map to the calibration coefficients. In another exemplary method, the LED spectral distribution may be input into a mathematical model that could be, e.g., a Beer's Lambert expression for RatRat to SpO2 or e.g., may be based on a MonteCarlo homogenous tissue model. The output parameters may then be mapped to the calibration coefficients.

These and other techniques will be for fully described below:

As we have noted above, theoretically the LED spectral irradiance distribution should follow a Maxwell-Boltzman distribution, shown below:

$$f(\lambda) = \sqrt{\frac{hc}{\lambda} - E_g} \, e^{\left(-\frac{hc}{\lambda kT}\right)}$$

Here, h is Planck's constant, c is the speed of light, $\lambda$ is the wavelength of light, k is the Boltzmann constant, T is temperature and Eg is the bandgap energy.

Figure 8:
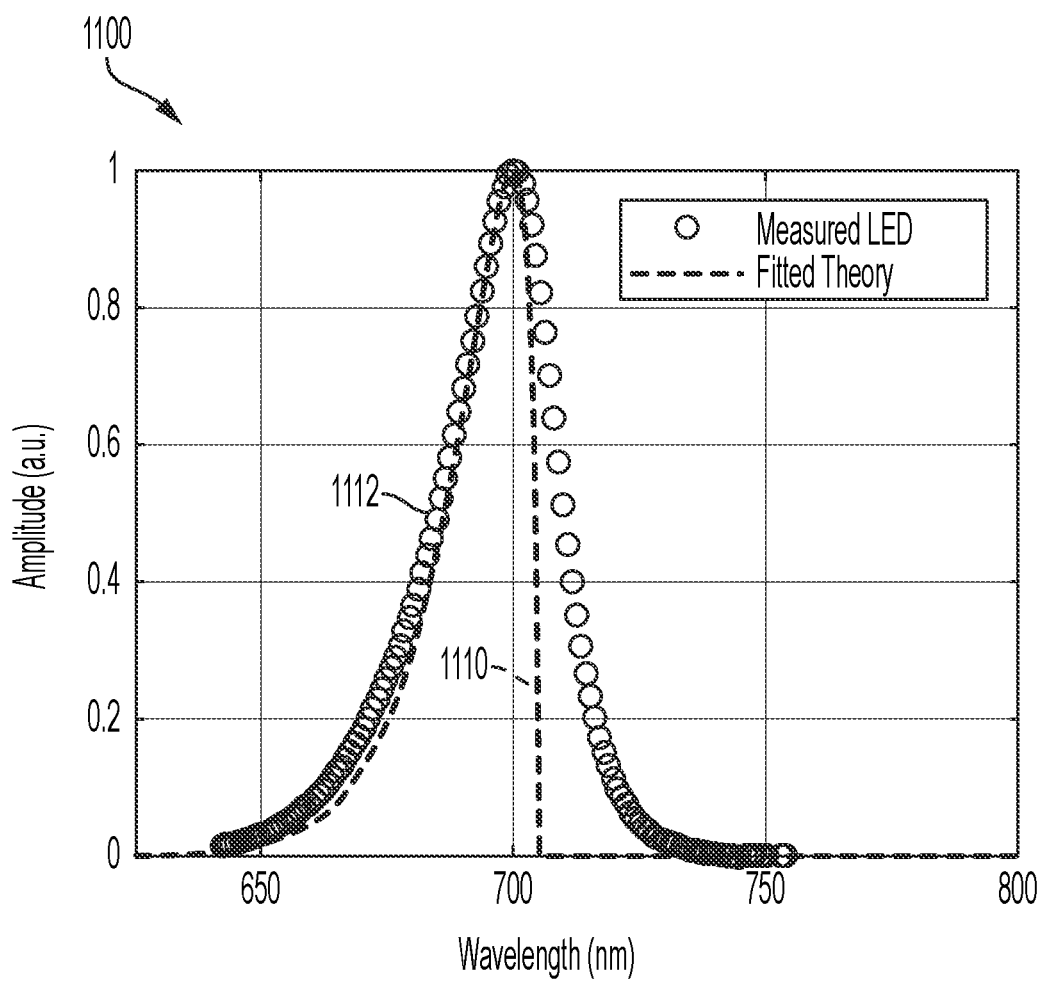
FIG. 8 is an exemplary graph showing fitting of a Maxwell-Boltzmann distribution to a measured red LED.

FIG. 8 shows at 1100 a best fit 1110 of the Maxwell-Boltzmann distribution to a measured red LED 1112 at a predetermined temperature and bandgap energy. The equation fits to the shorter wavelengths with reasonable accuracy but fails to capture the distribution at the longer wavelengths. Instead of utilizing the theoretical distribution, various non-symmetrical distribution functions may also be used and compared to the empirical data.

For example, logistic power peak may be utilized according to the following equation:

$$f(\lambda) = \frac{A}{S}\left(1 + e^{-\frac{\lambda - C + W\ln(S)}{S}}\right)^{-S-1} S^{-S}(S+1)^{S+1} e^{-\frac{\lambda - C + W\ln(S)}{S}}$$

Here, A is used to fit the amplitude, S models the skewness, W is the full-width at half the maximum (FWHM), and C models the peak wavelength. To fit the measured data, Matlab's nonlinear fit function may be used, with the fit is shown generally at 1200 in FIG. 9A and the error to the fit shown generally at 1300 in FIG. 9B.

The fitted function parameters are shown in Table 1, below; and Table 2 shows the difference between the fitted distribution and measured distribution for peak wavelength, FWHM, centroid and center wavelength.

TABLE 1

Fitted parameters for the logistic power peak function

| Parameter | Fit Value |
|---|---|
| A | 0.6695 |
| C | 712.6 |
| W | 5.253 |
| S | 4.657 |

TABLE 2

Comparison of the fitted distribution to the measured spectral irradiance for peak, center, FWHM, and centroid wavelength.

| Parameter | Measured (nm) | Fitted (nm) | Error (nm) |
|---|---|---|---|
| Peak | 700.0 | 699.9 | −0.1 |
| Center | 697.5 | 697.6 | 0.1 |
| FWHM | 25.07 | 25.37 | 0.3 |
| Centroid | 694.4 | 693.4 | −1.0 |

Figure 9B:
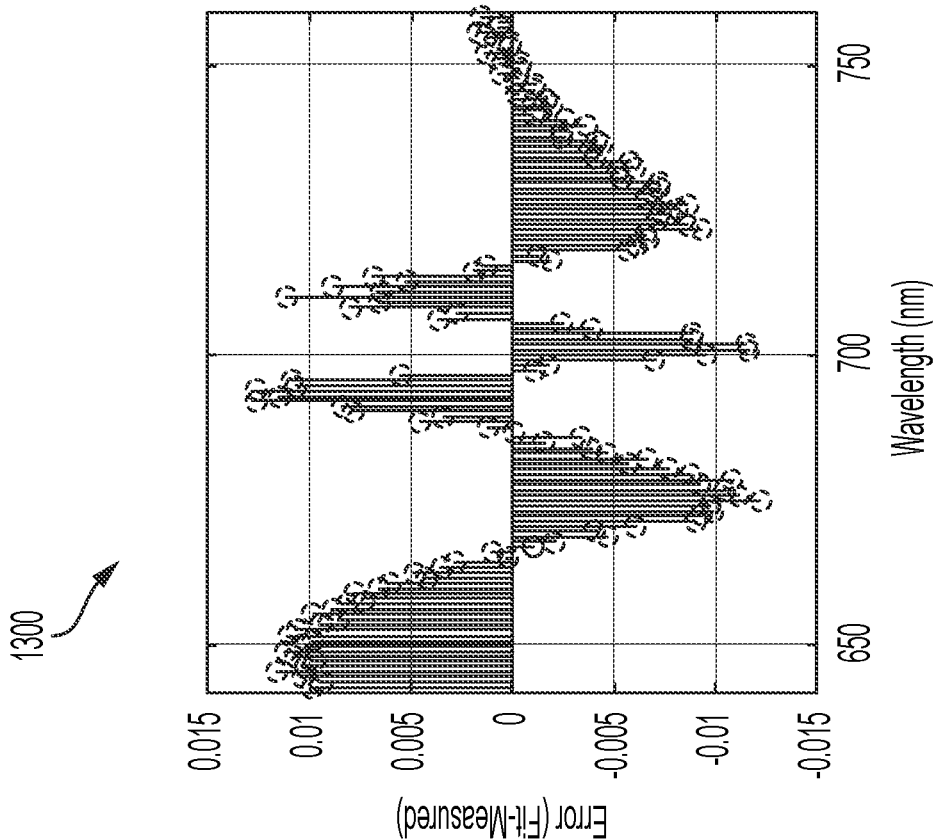
FIG. 9B is an exemplary graph showing the error of the fit in FIG. 9A.
Figure 9A:
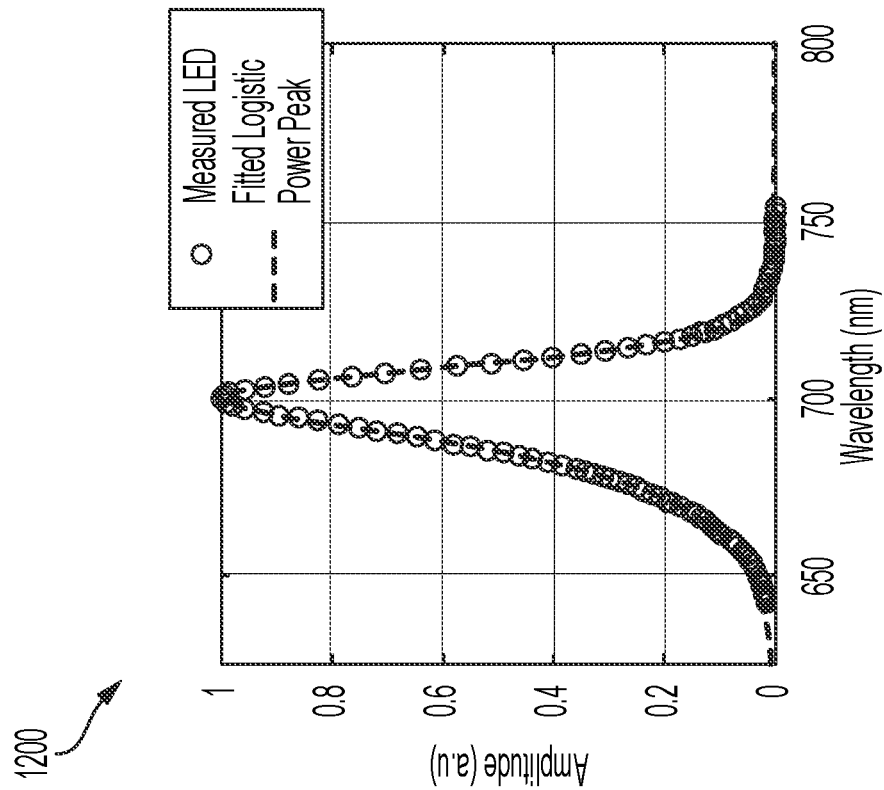
FIG. 9A is an exemplary graph showing fitting of a logistic power peak function to LED distribution.

As can be seen from FIG. 9A, the logistic power peak function fits to the LED distribution well, capturing the asymmetry. FIG. 9B is an exemplary graph showing the error of the fit in FIG. 9A. The difference (error) between the fitted distribution compared to the measured was 1 nm for the centroid and −0.1 nm the for peak.

In another example, asymmetric double sigmoidal may be utilized, with the functional form of the logistic power peak shown in the following equation:

$$f(\lambda) = \frac{A}{1+e^{\frac{\lambda-C+W/2}{S_1}}}\left(1 - \frac{1}{1+e^{\frac{\lambda-C-W/2}{S_2}}}\right)$$

Figure 10B:
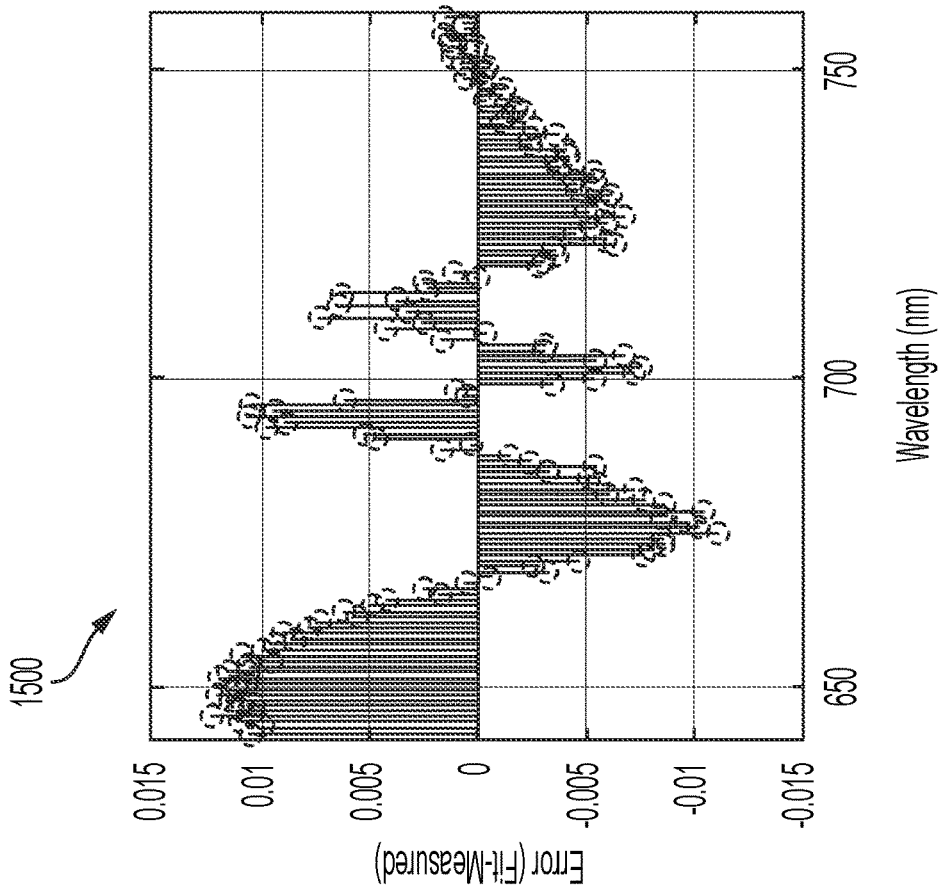
FIG. 10B is an exemplary graph showing the error of the fit in FIG. 10A.

Here, A is used to fit the amplitude, $S_1$ models the skewness for wavelengths shorter than peak, $S_2$ models the skewness for wavelengths longer than peak, W models the full-width at half the maximum, and C models the peak wavelength. To fit the measured data, Matlab's nonlinear fit function may be used, with the fit shown generally at 1400 in FIG. 10A and the error to the fit shown generally at 1500 in FIG. 10B. The fitted function parameters are shown in Table 3; with Table 4 showing the difference between the fitted distribution and measured distribution for peak wavelength, FWHM, centroid and center wavelength.

TABLE 3

Fitted parameters for the asymmetric double sigmoidal function

| Parameter | Fit Value |
|---|---|
| A | 22.98 |
| C | 721.5 |
| W | −35.2 |
| $S_1$ | 14.25 |
| $S_2$ | 4.226 |

TABLE 4

Comparison of the fitted distribution to the measured spectral irradiance for peak, center, FWHM, and centroid wavelength.

| Parameter | Measured (nm) | Fitted (nm) | Error (nm) |
|---|---|---|---|
| Peak | 700 | 699.9 | −0.1 |
| Center | 697.5 | 697.6 | 0.1 |
| FWHM | 25.07 | 25.17 | 0.1 |
| Centroid | 694.4 | 693.4 | −1.0 |

Figure 10A:
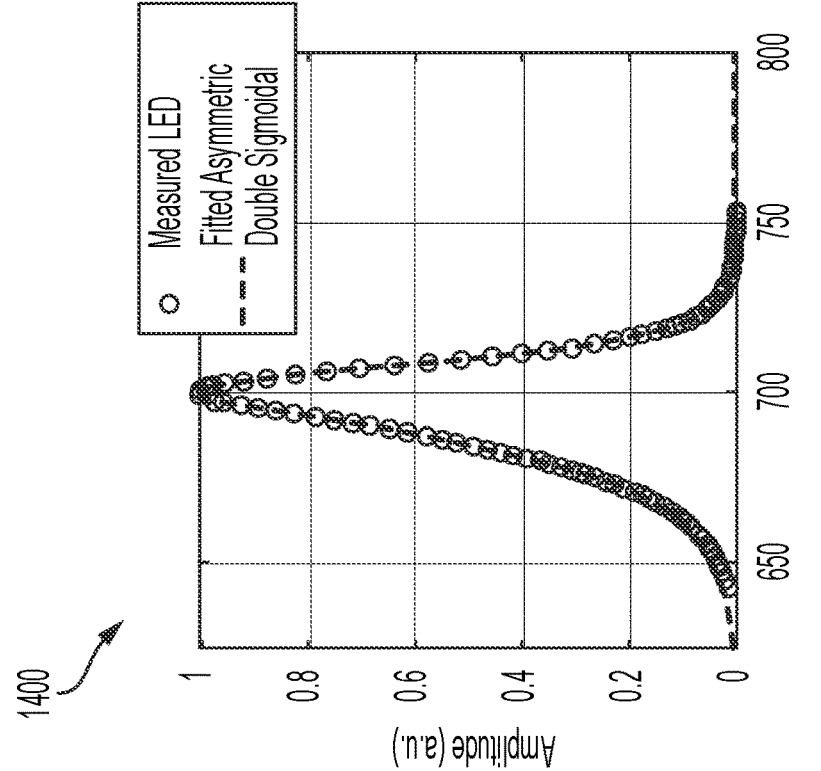
FIG. 10A is an exemplary graph showing fitting to LED distribution using asymmetric double sigmoidal equation and Matlab's nonlinear fit function.

As may be seen from FIG. 10A, the asymmetric double sigmoidal function fits to the LED distribution well, capturing the asymmetry. The difference (error) between the fitted distribution compared to the measured was 1 nm for the centroid and −0.1 nm the for peak.

In other exemplary embodiments, the distribution may be fit by summing Gaussian distributions, with the functional form of the sum of Gaussians shown from the following equation:

$$f(\lambda) = \sum_{i=1}^{3} A_i e^{\frac{\lambda-C_i}{W_i}}$$

Figure 11B:
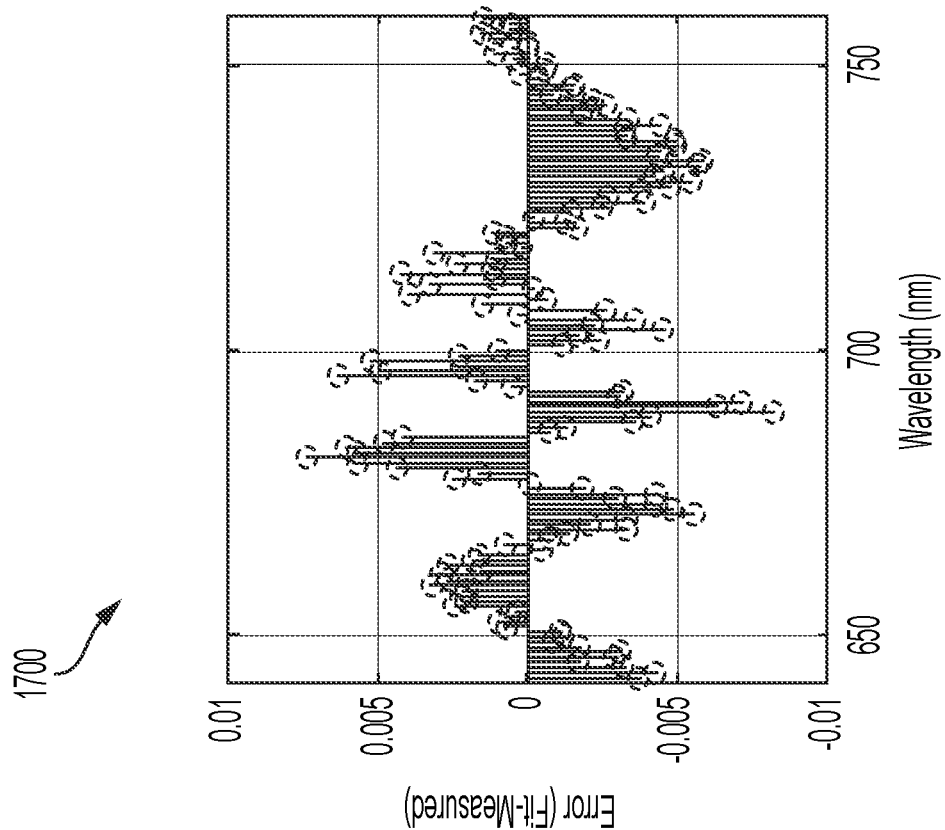
FIG. 11B is an exemplary graph showing the error of the fit in FIG. 11A.

Here, $A_i$ is used to fit the amplitude of the ith Gaussian, $W_i$ models the full-width at half the maximum of the ith Gaussian, and $C_i$ models the peak wavelength of the ith Gaussian. To fit the measured data, Matlab's nonlinear fit function may be used, with the fit shown generally at 1600 in FIG. 11A and the error to the fit shown generally at 1700 in FIG. 11B. The fitted function parameters are shown in Table 5; with Table 6 showing the difference between the fitted distribution and measured distribution for peak wavelength, FWHM, centroid and center wavelength.

TABLE 5

Fitted parameters for the logistic power peak function

| Parameter | Fit Value |
|---|---|
| $A_1$ | 0.103 |
| $C_1$ | 671.8 |
| $W_1$ | 19.9 |
| $A_2$ | 0.415 |
| $C_2$ | 701.6 |
| $W_2$ | 8.87 |
| $A_3$ | 0.615 |
| $C_3$ | 695.9 |
| $W_3$ | 180.0 |

TABLE 6

Comparison of the fitted distribution to the measured spectral irradiance for peak, center, FWHM, and centroid wavelength.

| Parameter | Measured (nm) | Fitted (nm) | Error (nm) |
|---|---|---|---|
| Peak | 700.0 | 699.9 | −0.1 |
| Center | 697.5 | 697.5 | 0 |
| FWHM | 25.07 | 25.18 | 0.1 |
| Centroid | 694.4 | 694.2 | −0.2 |

Figure 11A:
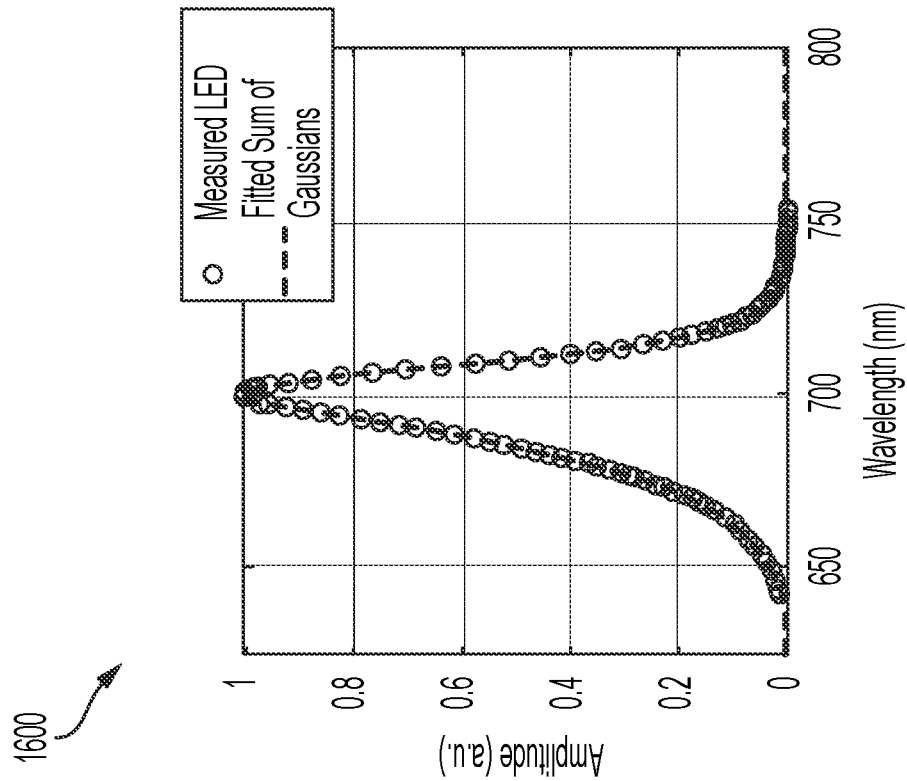
FIG. 11A is an exemplary graph showing fitting to LED distribution using summing of Gaussian distributions and Matlab's nonlinear fit function.

As may be seen from FIG. 11A, the sum of Gaussians method fits to the LED distribution well, capturing the asymmetry. The difference (error) between the fitted distribution compared to the measured was −0.2 nm for the centroid and −0.1 nm the for peak.

The above provides exemplary distribution functions, including: logistic peak power; asymmetric double sigmoidal; and sum of Gaussians, each of which advantageously fit the spectral distribution well, accounting for longer wavelengths and accurately capturing the measured distribution. Fitting the measured spectral distribution to three Gaussian functions was found to accurately reproduce the peak, center and centroid wavelengths with a small error (0.1 nm) in FWHM. The asymmetric double sigmoidal function also has the benefit of modeling the skewness for shorter and longer wavelengths, relative to the peak, with independent parameters ($S_1$ and $S_2$).

In some embodiments, the physiological monitoring system may comprise a sensor configured to store algorithm configuration data, which may be algorithm coefficient(s) and generate a photoplethysmography (PPG) signal. A port (e.g., a bi-directional input/output) may be communicatively coupled to the sensor and may be configured to receive an algorithm configuration data and the PPG signal from the sensor. At least one processor may be configured to configure or modify at least a part of the first algorithm based upon the algorithm configuration data received by a monitor from the sensor and to execute the first algorithm as configured or modified to determine at least one physiological parameter of a subject based on the PPG signal. The at least one processor may further be configured to delete the algorithm configuration data from the monitor, or deactivate the configuration or modifications of the first algorithm after the sensor becomes communicatively disconnected from the port. By providing algorithm configuration data on the sensor, new algorithm configurations may be provided to the monitor without the need for afield update of all installed monitors. Rather, the sensor may carry the most updated configuration data to the monitor for execution during patient monitoring, providing a higher quality calculation of patient parameters than otherwise would be possible without the algorithm configuration data. Additionally, different types of sensors may have different capabilities, which can be reflected in the algorithm configuration data they carry.

In some embodiments, a physiological sensor may be provided. The physiological sensor may comprise at least one light source configured to generate a light signal, at least one light detector configured to receive the light signal after the light signal has been attenuated by body tissue of a subject, and non-transitory memory (e.g., integrated memory) configured to store algorithm configuration data. The physiological sensor may further comprise a port. The port may comprise a bi-directional input/output port, a wireless interface, NFC (near field communication) interface, RFID link, one-wire interface, I2C, SPI, UART, or any other type of a port or communication interface. In some embodiments, the port may also have other capabilities. For example, the port may comprise an output of a photodetector capable of transmitting PPG data. The port may be configured to transmit the light signal to a physiological monitor that is communicatively coupled to the port and to transmit algorithm configuration data to the physiological monitor, which is configured to execute an executable code segment stored on the physiological monitor, as configured or modified by the algorithm configuration data received from the sensor to determine at least one physiological parameter of the subject based on the light signal. The algorithm configuration data may be deleted, or algorithm configurations or modifications may be deactivated after the physiological monitor becomes communicatively disconnected from the sensor. In some embodiments, the physiological monitor may become communicatively disconnected from the sensor, for example, when the sensor is physically disconnected form the physiological monitor, or when the sensor is moved out of the wireless range of the physiological monitor.

In some embodiments a physiological monitoring system may be provided. The physiological monitoring system may comprise a sensor that is configured to store algorithm configuration data and generate a photoplethysmographic (PPG) signal. The physiological monitoring system may further comprise a physiological monitor. The physiological monitor may comprise a port that is communicatively coupled to the sensor and is configured to receive the algorithm configuration data and the PPG signal from the sensor. The physiological monitor may comprise non-transitory memory configured to store a sequence of ordered algorithm stages wherein one of the algorithm stages comprises a configurable algorithm stage, the configurable algorithm stage comprising a plurality of alternative executable code segments.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A method for calibrating a medical device, the method comprising:
providing a sensor having at least one light-emitting diode (LED) configured for LED emission through tissue and having a memory device;
characterizing a spectrum distribution of the LED emission of the at least one LED;
mapping the characterized spectrum distribution to at least one calibration coefficient, wherein the at least one calibration coefficient comprises at least one gamma coefficient;
storing the at least one calibration coefficient in the memory device;
transmitting the at least one calibration coefficient from the memory device to a patient monitor to cause modifications to a sensing signal algorithm based on the at least one calibration coefficient while the sensor is communicatively connected to the patient monitor; and
deleting the at least one calibration coefficient from the patient monitor or deactivating the modifications to the sensing signal algorithm after the sensor is communicatively disconnected from the patient monitor.

2. A method in accordance with claim 1, wherein the LED emission provides an asymmetric distribution, and wherein the mapping of the characterized spectrum distribution to the at least one calibration coefficient reflects such asymmetric distribution.

3. A method in accordance with claim 1, wherein a full spectrum distribution of the at least one LED is characterized, with the mapping of the characterized full spectrum distribution to the at least one calibration coefficient reflecting the full spectrum distribution.

4. A method in accordance with claim 1, wherein the mapping of the characterized spectrum distribution to the at least one gamma coefficient includes de-convolving LED distribution into a number of Gaussian distributions and using the number of Gaussian distributions to map the characterized spectrum distribution to the at least one gamma coefficient.

5. A method in accordance with claim 1, wherein the mapping of the characterized spectrum distribution to the at least one gamma coefficient includes fitting an LED distribution to a logistic power peak and using fitted parameters to map the characterized spectrum distribution to the at least one gamma coefficient.

6. A method in accordance with claim 1, wherein the mapping of the characterized spectrum distribution to the at least one gamma coefficient includes fitting an LED distribution to an asymmetric double sigmoidal and mapping the characterized spectrum distribution to the at least one gamma coefficient.

7. A method in accordance with claim 1, wherein the mapping of the characterized spectrum distribution to the at least one gamma coefficient includes characterizing distribution skewness.

8. A method in accordance with claim 1, wherein the mapping of the characterized spectrum distribution to the at least one gamma coefficient includes measuring a peak wavelength, a full width at half maximum (FWHM), or both, and a centroid wavelength and mapping to the at least one gamma coefficient.

9. A method in accordance with claim 1, wherein the mapping of the characterized spectrum distribution to the at least one gamma coefficient includes integrating an LED distribution with a blood absorption curve and mapping to the at least one gamma coefficient.

10. A method of claim 1, comprising executing the sensing signal algorithm with the modifications to determine at least one physiological parameter.

11. A system for calibrating a medical device, comprising:
a medical sensor comprising:
a memory device that stores configuration data for the medical sensor; and
at least one light-emitting diode (LED) configured for LED emission through tissue and configured to generate a sensing signal, wherein the LED emission provides an asymmetric distribution;
a medical monitor to communicatively couple to the medical sensor and to receive the configuration data from the medical sensor, the medical monitor configured to:
adjust a sensing signal algorithm with modifications based upon the configuration data, wherein the configuration data includes at least one calibration coefficient based on characterization of a spectrum distribution of the LED emission and mapping of the characterized spectrum distribution to the at least one calibration coefficient, wherein the mapping reflects the asymmetric distribution; and
delete the configuration data or deactivate the modifications to the sensing signal algorithm in response to communicatively decoupling from the medical sensor.

12. A system in accordance with claim 11, wherein the at least one calibration coefficient comprises at least one gamma coefficient.

13. A system in accordance with claim 11, wherein a full spectrum distribution of the at least one LED is characterized, with mapping of the characterized full spectrum distribution to the at least one calibration coefficient reflecting the full spectrum distribution.

14. A system in accordance with claim 11, wherein the medical monitor executes the adjusted sensing signal algorithm with the modifications to determine at least one physiological parameter.

15. A system in accordance with claim 12, wherein the mapping of the characterized spectrum distribution to the at least one gamma coefficient includes de-convolving LED distribution into a number of Gaussian distributions and using the number of Gaussian distributions to map the characterized spectrum distribution to the at least one gamma coefficient.

16. A system in accordance with claim 12, wherein the mapping of the characterized spectrum distribution to the at least one gamma coefficient includes fitting an LED distribution to a logistic power peak and using fitted parameters to map the characterized spectrum distribution to the at least one gamma coefficient.

17. A system in accordance with claim 12, wherein the mapping of the characterized spectrum distribution to the at least one gamma coefficient includes fitting an LED distribution to an asymmetric double sigmoidal and mapping the characterized spectrum distribution to the at least one gamma coefficient.

18. A system in accordance with claim 12, wherein the mapping from the characterized spectrum distribution to the at least one gamma coefficient includes characterizing distribution skewness.

19. A system in accordance with claim 12, wherein the mapping of the characterized spectrum distribution to the at least one gamma coefficient includes measuring a peak wavelength, a full width at half maximum (FWHM), or both, and a centroid wavelength and mapping to the at least one gamma coefficient.

20. A system in accordance with claim 12, wherein the mapping of the characterized spectrum distribution to the at least one gamma coefficient includes integrating an LED distribution with a blood absorption curve and mapping to the at least one gamma coefficient.

* * * * *